United States Patent
Yum et al.

(10) Patent No.: US 11,147,858 B2
(45) Date of Patent: Oct. 19, 2021

(54) PHARMACEUTICAL COMPOSITION FOR TREATING INFLAMMATORY BOWEL DISEASE

(71) Applicant: GENOFOCUS, INC., Daejeon (KR)

(72) Inventors: Do Young Yum, Daejeon (KR); Jeong Hyun Kim, Seongnam-si (KR); Jae Gu Pan, Sejong (KR); Eui Joong Kim, Daejeon (KR); Ji Eun Kang, Icheon-si (KR)

(73) Assignee: GENOFOCUS, INC., Daejeon (KR)

( * ) Notice: Subject to any disclaimer, the term of this patent is extended or adjusted under 35 U.S.C. 154(b) by 221 days.

(21) Appl. No.: 16/464,592

(22) PCT Filed: Dec. 26, 2018

(86) PCT No.: PCT/KR2018/016654
§ 371 (c)(1),
(2) Date: May 28, 2019

(87) PCT Pub. No.: WO2020/050460
PCT Pub. Date: Mar. 12, 2020

(65) Prior Publication Data
US 2020/0316177 A1  Oct. 8, 2020

(30) Foreign Application Priority Data

Sep. 4, 2018  (KR) .................. 10-2018-0105592

(51) Int. Cl.
| | |
|---|---|
| *A61K 38/44* | (2006.01) |
| *A61P 37/06* | (2006.01) |
| *A61P 1/00* | (2006.01) |
| *A61K 47/46* | (2006.01) |

(52) U.S. Cl.
CPC ............ *A61K 38/446* (2013.01); *A61K 47/46* (2013.01); *A61P 1/00* (2018.01); *A61P 37/06* (2018.01)

(58) Field of Classification Search
None
See application file for complete search history.

(56) References Cited

U.S. PATENT DOCUMENTS 10,751,393 B2 * 8/2020 Yum .................. C12N 1/20

FOREIGN PATENT DOCUMENTS

| KR | 2008-0083840 | 9/2008 |
|---|---|---|
| KR | 2012-0111091 | 10/2012 |
| KR | 2014-0053950 | 5/2014 |
| KR | 2014-0143497 | 12/2014 |
| KR | 10-1814035 | * 1/2018 |
| KR | 2018-0075445 | 7/2018 |

OTHER PUBLICATIONS

Kang, J. et al. Dietary Supplementation with a Bacillus Superoxide Dismutase Protects Against Gamma Radiation Induced Oxidative Stress . . . J of Crohn's Colitis 12(7)860-869, Jun. 28, 2018. (Year: 2018).*
International Search Report and Written Opinion of PCT/KR2018/016654, dated May 16, 2019, 12 pages.
Kang, "Dietary Supplementation With a Bacillus Superoxide Dismutase Protects Against γ-Radiation-induced Oxidative Stress and Ameliorates Dextran Sulphate Sodium-induced Ulcerative Colitis in Mice", Journal of Crohn's & Colitis, Jun. 28, 2018, pp. 860-869.

* cited by examiner

*Primary Examiner* — Ralph J Gitomer
(74) *Attorney, Agent, or Firm* — Hamre, Schumann, Mueller & Larson, P.C.

(57) ABSTRACT

The present invention relates to a pharmaceutical composition for preventing or treating inflammatory disease, which contains, as an active ingredient, a *Bacillus amyloliquefaciens* GF423 strain, a superoxide dismutase high-producing *Bacillus amyloliquefaciens* GF424 mutant strain, a superoxide dismutase (SOD) derived from one of these strains, or both the strain and the SOD. The superoxide dismutase derived from the *Bacillus amyloliquefaciens* GF423 strain (KCTC 13222BP), which is the active ingredient of the present invention, effectively suppresses or degrades reactive oxygen species, and thus has the effect of fundamentally preventing the causes of inflammatory bowel disease caused by reactive oxygen species. Therefore, the composition of the present invention may be developed into various products, including excellent drugs and health functional foods for preventing or treating inflammatory bowel disease.

10 Claims, 6 Drawing Sheets

Specification includes a Sequence Listing.

PHARMACEUTICAL COMPOSITION FOR TREATING INFLAMMATORY BOWEL DISEASE

TECHNICAL FIELD

The present invention relates to a pharmaceutical composition for preventing or treating inflammatory bowel disease, and more particularly to a pharmaceutical composition and food for preventing or treating inflammatory bowel disease, which contain a *Bacillus amyloliquefaciens* GF423 strain, a superoxide dismutase (SOD) high-producing *Bacillus amyloliquefaciens* GF424 mutant strain, or an SOD derived from one of these strains.

BACKGROUND ART

Inflammatory bowel disease (IBD) is an intractable disease that causes chronic inflammation or ulceration in the mucosa of the large intestine and the small intestine, causes diarrhea and bloody stools continuously over a long period of time, and recurs repeatedly. The definite cause of the disease has not been found.

The prevalence and incidence of inflammatory bowel disease have increased in developed countries. Although inflammatory bowel disease (IBD) is not a life-threatening fatal disease, it significantly reduces the quality of life due to symptoms such as pain, vomiting, and diarrhea. Furthermore, 0.5% to 20% of annual inflammatory bowel disease patients are accompanied by severe complications that increase the risk of colorectal cancer. Therefore, it is essential to treat inflammatory bowel disease at a proper time, but a drug capable of fundamentally treating inflammatory bowel disease (IBD) has not yet been developed.

The current therapy for inflammatory bowel disease relies on the use of sulfasalazine, corticosteroids, immunosuppressive agents, such as azatriopine, and biological therapy represented by anti-TNFα as the mainstream treatment for suppressing aberrant immune responses and inflammatory responses. However, adverse effects associated with these drugs over prolonged treatment periods and the relapse rate limit their use. For example, sulfasalazine may exacerbate colitis, causing diarrhea, abdominal cramps and discomfort. Antibiotics, one of the commonly used therapies, have adverse effects that kill not only pathogens but also intestinal beneficial bacteria that are absolutely critical to human health. In addition, damage to intestinal microorganisms caused by antibiotics cannot be easily recovered even after several years, and may lead to chronic diseases such as hypertension, diabetes, atopy and the like. Furthermore, these drugs act as a mechanism to inhibit immune function and, thus, are hardly administered over a long period of time. When these drugs are administered over a long period of time, they may cause adverse effects, including nausea, vomiting, indigestion, anorexia, and headache, as well as hypersensitivity reaction with leukopenia, skin rash, fever, pancreatitis, hepatitis, hemolytic anemia, and bone marrow suppression. Furthermore, intestinal damage due to complications occurs during drug treatment, and thus more than 70% of patients undergo surgery at least once. Therefore, there is a need to develop therapeutic agents for effectively treating inflammatory bowel disease without causing adverse effects.

Recently, as several studies have recognized that imbalance between protective intestinal microorganisms and harmful intestinal microorganisms is one of the important causes of inflammatory bowel disease, there has been much interest in developing probiotic compositions that can improve therapeutic effects against inflammatory bowel disease. As one example, Korean Patent Application Publication No. 2014-0053950 discloses a method of treating inflammatory bowel disease probiotic microbial strains including *Pediococcus*.

Meanwhile, other causes of inflammatory bowel disease include an increase in reactive oxygen species (ROS). Reactive oxygen species are clearly associated with inflammatory bowel disease. Once immune activation, such as inflammation, has occurred, reactive oxygen species may become a major cause of tissue damage and fibrosis. A proper amount of reactive oxygen species in vivo plays an important role in signal transduction, but the excessive increase in intracellular reactive oxygen species by external stress stimuli may cause diseases. Korean Patent Application Publication No. 2018-0075445 discloses a pharmaceutical composition for preventing and treating inflammatory bowel disease, which contains an *E. coli* strain that produces catalase having an excellent ability to degrade hydrogen peroxide among reactive oxygen species. However, these formulations have insufficient effects against inflammatory bowel disease, even though the adverse effects thereof were somewhat reduced. Therefore, it is required to develop a drug having less adverse effects while having better effects.

DISCLOSURE

Technical Problem

The present invention has been conceived to overcome the above-described limitations of the prior art, and an object of the present invention is to provide a novel pharmaceutical composition for preventing or treating inflammatory bowel disease, which contains, as a main component, a superoxide dismutase (SOD) derived from a *Bacillus amyloliquefaciens* GF423 strain (KCTC 13222BP).

Another object of the present invention is to provide a pharmaceutical composition for preventing or treating inflammatory bowel disease, which contains the *Bacillus amyloliquefaciens* GF423 strain.

Still another object of the present invention is to provide a pharmaceutical composition for preventing or treating inflammatory bowel disease, which contains a *Bacillus amyloliquefaciens* GF424 mutant strain.

Still another object of the present invention is to provide a pharmaceutical composition for preventing or treating inflammatory bowel disease, which contains: one or more of the *Bacillus amyloliquefaciens* GF423 strain and the *Bacillus amyloliquefaciens* GF424 mutant strain; and a superoxide dismutase derived from these strains.

Yet another object of the present invention is to provide a health functional food useful for preventing or ameliorating inflammatory bowel disease, which contains a superoxide dismutase derived from the *Bacillus amyloliquefaciens* GF423 strain.

Technical Solution

Provided is a pharmaceutical composition for preventing or treating inflammatory bowel disease, which contains a superoxide dismutase derived from a *Bacillus amyloliquefaciens* GF423 strain (KCTC 13222BP).

Provided is a pharmaceutical composition for preventing or treating inflammatory bowel disease, which contains a *Bacillus amyloliquefaciens* GF423 strain (KCTC 13222BP)

or a superoxide dismutase high-producing *Bacillus amyloliquefaciens* GF424 mutant strain (accession number: KCTC 13227BP).

Provided is a pharmaceutical composition for preventing or treating inflammatory bowel disease, which contains: at least one of a *Bacillus amyloliquefaciens* GF423 strain (KCTC 13222BP) and a superoxide dismutase high-producing *Bacillus amyloliquefaciens* GF424 mutant strain (accession number: KCTC 13227BP); and a superoxide dismutase derived from the *Bacillus amyloliquefaciens* GF423 strain (KCTC 13222BP).

In the present invention, the *Bacillus amyloliquefaciens* GF423 or the *Bacillus amyloliquefaciens* GF424 may be one or more selected from the group consisting of a strain, a spore of the strain, a culture of the strain, a concentrate thereof, an extract thereof, and a dried product thereof.

Provided is a food useful for preventing or ameliorating inflammatory bowel disease, which contains: at least one of a *Bacillus amyloliquefaciens* GF423 strain (KCTC 13222BP) and a superoxide dismutase high-producing *Bacillus amyloliquefaciens* GF424 mutant strain (accession number: KCTC 13227BP); and a superoxide dismutase derived from the *Bacillus amyloliquefaciens* GF423 strain (KCTC 13222BP).

Advantageous Effects

The superoxide dismutase derived from the *Bacillus amyloliquefaciens* strain, which is the active ingredient of the pharmaceutical composition of the present invention, can fundamentally prevent the causes of inflammatory disease by reducing oxidative stress and inflammatory responses in the inflammatory bowel disease, and thus can effectively prevent or treat the inflammatory bowel disease. Therefore, the pharmaceutical compositions of the present invention can be developed into various products, including excellent drugs and health functional foods for preventing or treating inflammatory bowel disease.

A superoxide dismutase, which is produced by the strain of the present invention, the superoxide dismutase high-producing *Bacillus amyloliquefaciens* mutant strain, and a superoxide dismutase which is produced by the mutant strain, can more effectively reduce oxidative stress and inflammatory responses than an SOD derived from plants such as melon.

According to the present invention, mass culture of cells by microbial suspension, mass production, and enzyme recovery are possible, and thus an SOD showing an excellent effect against inflammatory bowel disease compared to an SOD extracted from melon in a conventional art can be produced at low costs and in high yield. In addition, the overall production process can be performed under highly controlled conditions, and thus the SOD is more economic and efficient than the melon-derived SOD.

DESCRIPTION OF DRAWINGS

FIG. 6(A) is a graph showing the level of the proinflammatory cytokine TNF-α in mouse serum;

FIG. 6(B) is a graph showing the level of the proinflammatory cytokine TNF-1β in mouse serum; and FIG. 6(C) is a graph showing the level of the proinflammatory cytokine IL6 in mouse serum.

BEST MODE

Figures 1, 2:
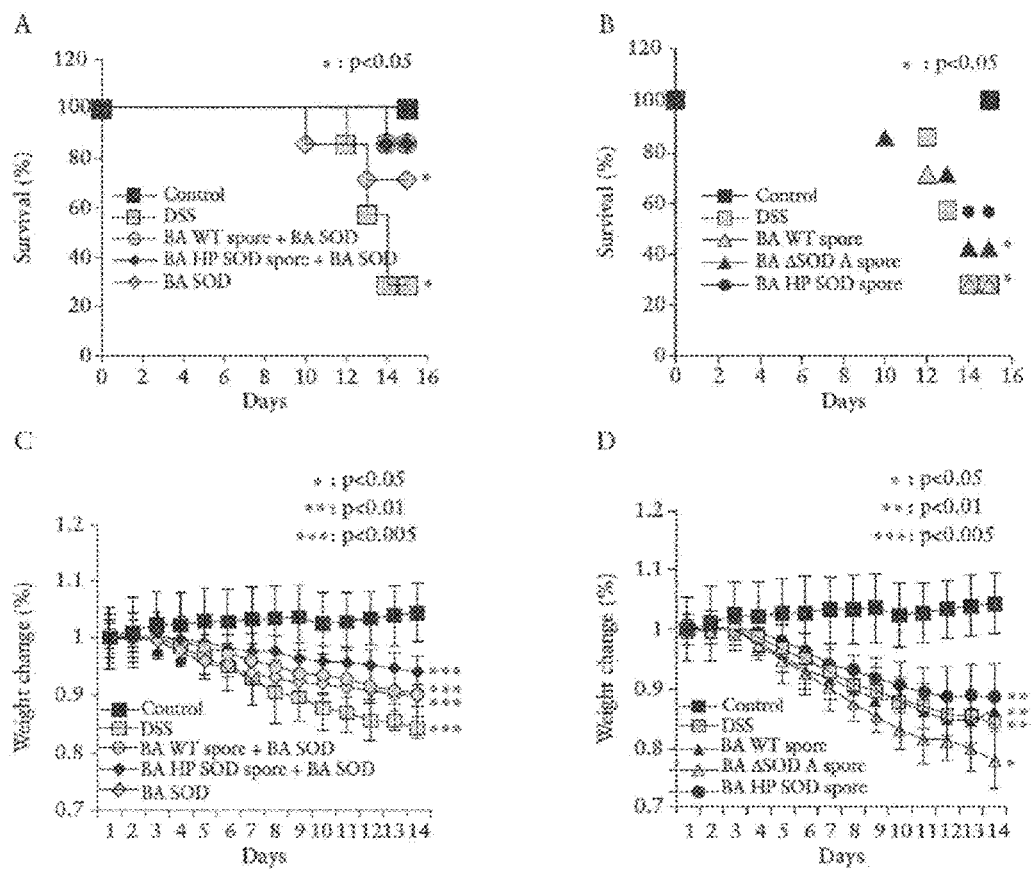
FIG. 1 shows a comparison between the amino acid sequence of SodA derived from *Bacillus amyloliquefaciens* GF423 and the amino acid sequences of *Bacillus amyloliquefaciens* FZB42 and *Bacillus subtilis* 168. The active positions of *Bacillus subtilis* SodA are indicated by dots below the sequence.
FIG. 2 depicts graphs showing the survival rate (A and B) and weight change (C and D) of mice after administration of various test strains or SOD.

The present invention will be described in greater detail below with reference to the accompanying drawings.

As used herein, the term "treatment" or "treating" refers to the medical management of a patient with the intent to cure, ameliorate, stabilize or prevent a pathological condition or disorder (e.g., inflammatory bowel disease). This term includes active treatment, i.e., treatment directed specifically toward the improvement of a pathological condition, and also includes causal treatment, i.e., treatment directed toward removal of the cause of the associated pathological condition. In addition, this term includes palliative treatment, i.e., treatment designed for the relief of symptoms rather than the curing of the pathological condition; preventative treatment, i.e., treatment directed to minimizing or partially or completely inhibiting the development of the associated pathological condition; and supportive treatment, i.e., treatment employed to supplement another specific therapy directed toward the improvement of the associated disease, pathological condition or disorder.

As used herein, the terms "prevent," "preventing," and "prevention" refer to the total or partial inhibition of the development, recurrence, onset or spread of inflammatory bowel disease, which results from the administration of the pharmaceutical composition provided herein.

As used herein, the term "effective" or "therapeutically effective amount" of the composition or agent refers to a sufficient amount of an agent which provides the desired effect, such as reducing, preventing or slowing the progression of physical changes associated with inflammatory bowel disease in the bowel, or reducing, preventing or slowing the progression of symptoms resulting from them. The exact amount of agent required may vary from subject to subject depending on the species, age and general condition of the subject, mode of administration, and the like. However, an appropriate "effective amount" in any individual case may be determined by one of ordinary skill in the art using routine experimentation.

One aspect of the present invention is directed to a pharmaceutical composition for preventing or treating inflammatory bowel disease, which contains a superoxide dismutase derived from a *Bacillus amyloliquefaciens* GF423 strain (KCTC 13222BP). The superoxide dismutase has the amino acid sequence of SEQ ID NO: 1.

"Inflammatory bowel disease" is generally divided into ulcerative colitis (UC) and Crohn's disease (CD). Intestinal Behcet's disease, which is relatively common, may belong to inflammatory bowel disease. These diseases are different from each other in their clinical features, but they all take chronic courses, and their cause and pathophysiology are not known, and thus they are referred to as inflammatory bowel disease for convenience. Unlike ulcerative colitis, Crohn's disease can affect any part of the bowel. The most prominent feature of Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel, which is the cause of the disease. Most patients with Crohn's disease require surgery at some point, but subsequent relapse is common and continuous medical treatment is usual.

"Ulcerative colitis (UC)" afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic ulcerative colitis. The clinical features of UC may be highly variable, and the onset of the disease may be insidious or sudden, and may involve diarrhea, tenesmus, and recurrent rectal bleeding. Due to the fulminant onset of the disease in the entire colon, toxic megacolon, which is life-threatening, may occur. Signs other than the intestine may include arthritis, pyoderma gangrenosum, uveitis, and nodular erythema.

An imbalance between routine production and detoxification of reactive oxygen species ("ROS"), such as superoxides and free radicals, may result in oxidative damage to the cellular structure and machinery. In addition, intracellular reactive oxygen species are produced through the mitochondrial electron transport system. Gastrointestinal epithelial cells with induced oxidative stress induce apoptosis, or show changes such as mitochondrial DNA damage, an increase in vascular endothelial growth factor (VEGF), a decrease in antioxidant enzyme, and an increase in inflammatory response. A superoxide dismutase derived from the Bacillus amyloliquefaciens GF423 strain (KCTC 13222BP) of the present invention exhibits the effects of suppressing the production of reactive oxygen species, promoting the activation of antioxidant enzyme in the human body, and strengthening the overall antioxidant defense mechanism, thereby protecting the gastrointestinal wall from oxidative stress.

An SOD having an activity of preventing or treating inflammatory bowel disease can be extracted from a culture supernatant of the Bacillus amyloliquefaciens GF423 strain in the pharmaceutical composition for preventing or treating inflammatory bowel disease according to the present invention. First, a culture is obtained by culturing Bacillus amyloliquefaciens GF423 in a complex medium (pH 6.0 to 7.0) at 25 to 42° C. for 1 to 4 days. As the complex medium for culturing the Bacillus amyloliquefaciens GF423 strain, LB (Luria-Bertani) medium, ISP (International Streptomyces Project) medium, NA (nutrient agar) medium, BHI (brain heart infusion agar) medium, SDA (sabouroud dextrose agar) medium, PDA (potato dextrose agar) medium, NB (nutrient broth) medium, or the like may be used. Preferably, LB medium, ISP medium, BHI medium, SDA medium, or NB medium may be used.

The SOD is preferably separated by the following separation method, but is not limited thereto. When the culture is centrifuged to obtain a culture supernatant and the culture supernatant is filtered and concentrated, a culture supernatant extract can be obtained by optimally extracting an active substance for preventing or treating inflammatory bowel disease. For example, a culture of the Bacillus amyloliquefaciens GF423 strain is centrifuged, and the supernatant fraction is collected, pretreated by solid-phase extraction, and then separated and purified by chromatography. In this case, for the chromatography, C18 reverse-phase HPLC is preferably used, but is not necessarily limited thereto.

The pharmaceutical composition of the present invention may further contain a pharmaceutical agent exhibiting the effect of preventing or treating inflammatory bowel disease. The composition of the present invention may further contain a pharmaceutical agent known as a therapeutic agent against inflammatory bowel disease in order to co-administer this agent.

Another aspect of the present invention is directed to a pharmaceutical composition for preventing or treating inflammatory bowel disease, which contains an SOD high-producing Bacillus amyloliquefaciens GF424 mutant strain (accession number: KCTC 13227BP) obtained by artificially mutating the Bacillus amyloliquefaciens GF423 strain (KCTC 13222BP) or a wild-type Bacillus amyloliquefaciens GF423 strain using UV light. The Bacillus amyloliquefaciens GF423 strain has the same 16s rRNA gene nucleotide sequence as one or more of SEQ ID NOs: 2 to 10.

The pharmaceutical composition for preventing or treating inflammatory bowel disease according to the present invention may contain, as an active ingredient, any one or more selected from the group consisting of the Bacillus amyloliquefaciens GF423 strain or Bacillus amyloliquefaciens GF424 mutant strain, a spore of the strain, a culture of the strain, a concentrate thereof, an extract thereof, and a dried product thereof. The state of the strain may be a liquid state or a dried state, but is not limited thereto.

As used herein, the term "spore" refers to the reproductive cells of bacteria, or the like. For the purpose of the present invention, the spore means the reproductive cells of the Bacillus amyloliquefaciens GF423 strain or the Bacillus amyloliquefaciens GF424 mutant strain.

As used herein, the term "culture" refers to a product obtained after culturing the strain, and may be an undiluted culture containing cells or may be a cultured strain or cells obtained by removing or concentrating the culture supernatant. The composition of the culture may further contain not only components necessary for conventional Bacillus culturing, but also components that synergistically act on the growth of Bacillus, and the resulting composition may be easily selected by those skilled in the art.

As used herein, the term "concentrate" refers to one obtained by concentrating the culture.

As used herein, the term "extract" refers to one obtained by extraction from the culture or a concentrate thereof, and may include all an extract, a dried product obtained by drying a dilution or concentrate of the extract, or a crude product or purified product thereof, or a fraction obtained by fractionating the same.

As used herein, the term "dried product" refers to one obtained by drying the culture, a concentrate thereof, an extract thereof, or a fraction thereof. The drying method may be air drying, natural drying, spray-drying and freeze-drying, but is not limited thereto.

The strain and mutant strain of the present invention not only promote antioxidant defenses (increasing SOD, catalase and GPx activities), but also enhance cell resistance to oxidative stress. These strains may release cytosolic proteins, including SOD, into the gastrointestinal tract through the spore-forming life cycle. An SOD derived from the Bacillus amyloliquefaciens SOD is found extracellularly in liquid culture. This superoxide dismutase ameliorates intestinal inflammation by inhibiting apoptosis and promoting the proliferation and migration of epithelial cells. In addition, co-administration of a spore of the Bacillus amyloliquefaciens GF423 strain or a spore of the Bacillus amyloliquefaciens GF424 mutant strain and the SOD protein exhibits synergistic therapeutic effects.

The strains of the present invention may induce not only proinflammatory cytokines, for example, interleukin-1 (IL-1), IL-6, IL-12, tumor necrosis factor-alpha (TNF-α), and interferon-gamma (IFN-γ), but also anti-inflammatory cytokines such as transforming growth factor β and IL-10. IFN-γ and IL-12 may potently augment the functions of macrophages and NK cells, which may be a possible mechanism of their anti-carcinogenic and anti-inflammatory activities. On the other hand, the induction of IL-10 and transforming growth factor β is assumed to participate in the down-regulation of inflammation, since these cytokines can inhibit the functions of macrophages and T cells and promote the development of regulatory T cells. IL-10 has an anti-inflammatory effect and primarily acts to inhibit the Th1 response. IL-10 drives the generation of a CD4+ T-cell subset, designated T regulatory cells 1 (Tr1), thereby suppressing antigen-specific immune responses and actively down-regulating a pathological immune response in vivo.

The culture of the Bacillus amyloliquefaciens GF423 strain may be performed in a proper medium and under proper culture conditions known to those in the art. It is understood by those in the art that this culture process can be used by easily adjusting the same, according to the selected strain. Examples of this culture process include, but are not limited to batch, continuous culture and fed-batch culture processes. A variety of such culture processes are described, for example, in "Biochemical Engineering" by James M. Lee, Prentice-Hall International Editions, pp. 138-176.

The medium that is used in the culture of the strain of the present invention has to meet the culture conditions for a specific strain. A variety of microbial culture media are described, for example, in "Manual of Methods for General Bacteriology" by the American Society for Bacteriology, Washington D.C., USA, 1981. These media include various carbon sources, nitrogen sources and trace elements. The carbon sources include carbohydrates, such as glucose, lactose, sucrose, fructose, maltose, starch, and cellulose; fats such as soybean oil, sunflower oil, castor oil and coconut oil; fatty acids such as palmitic acid, stearic acid, and linoleic acid; alcohols such as glycerol and ethanol; and organic acids such as acetic acid. These carbon sources may be used alone or in combination.

The nitrogen sources include organic nitrogen sources, such as peptone, yeast extract, meat extract, malt extract, corn steep liquor and bean flour, and inorganic nitrogen sources, such as urea, ammonium sulfate, ammonium chloride, ammonium phosphate, ammonium carbonate and ammonium nitrate. These nitrogen sources may be used alone or in combination.

The media may additionally include, as phosphate sources, potassium dihydrogen phosphate, dipotassium hydrogen phosphate and corresponding sodium-containing salts as a phosphate source. In addition, the media may include metals such as magnesium sulfate or iron sulfate. Furthermore, amino acids, vitamins, proper precursors and the like may be added. These media or precursors may be added to the culture in a batch or continuous manner.

In addition, compounds, such as ammonium hydroxide, potassium hydroxide, ammonia, phosphoric acid, and sulfuric acid, may be added during culture in a suitable manner to adjust the pH of the culture medium. In addition, during culture, a defoaming agent such as fatty acid polyglycol ester may be used to suppress the formation of bubbles. Further, in order to maintain the culture medium under aerobic conditions, oxygen or an oxygen-containing gas (e.g., air) may be injected into the culture medium. The temperature of the culture medium is generally 20° C. to 45° C., preferably 25° C. to 40° C. Culture can be continued until the production of the SOD will reach the desired level. Preferably, the culture period is from 48 to 72 hours.

The pharmaceutical composition of the present invention contains, as an active ingredient, the strain in an amount of $1\times10^6$ to $1\times10^{12}$ live bacteria, preferably $1\times10^7$ to $1\times10^{11}$ live bacteria, based on the total weight of the composition, or contains a culture product having the same number of live bacteria. The Bacillus strains may be grown by a general culture method for Bacillus bacterial and recovered by a separation process such as centrifugation. The recovered strains may be dried by, for example, freeze-drying, and may be used as probiotics.

The pharmaceutical composition for preventing or treating inflammatory bowel disease according to the present invention may further contain a pharmaceutically acceptable carrier or excipient, in addition to the SOD derived from the Bacillus amyloliquefaciens GF423 strain (KCTC 13222BP) or the Bacillus amyloliquefaciens GF423 strain (KCTC 13222BP). In addition, it may be formulated with various additives, such as a binder, a coating agent and the like, which are pharmaceutically commonly used.

The pharmaceutical composition for preventing or treating IBD according to the present invention may contain a pharmaceutically acceptable carrier. For oral administration, the pharmaceutically acceptable carrier may include a binder, a lubricant, a disintegrant, an excipient, a solubilizer, a dispersing agent, a stabilizer, a suspending agent, a coloring agent, a flavoring agent, and the like. For injectable administration, the pharmaceutically acceptable carrier may include a buffering agent, a preservative, an analgesic, a solubilizer, an isotonic agent, a stabilizer, and the like. For topical administration, the pharmaceutically acceptable carrier may include a base, an excipient, a lubricant, a preservative, and the like. The pharmaceutical composition of the present invention may be formulated into a variety of dosage forms in combination with the aforementioned pharmaceutically acceptable carriers. For example, for oral administration, the pharmaceutical composition may be formulated in dosage forms such as tablets, troches, capsules, elixirs, suspensions, syrups, wafers, or the like. For injectable administration, the pharmaceutical composition may be formulated as a unit dosage ampoule or a multiple dosage form. In addition, the pharmaceutical composition may be formulated into solutions, suspensions, tablets, capsules, sustained-release preparations, or the like.

Meanwhile, examples of the carrier, excipient and diluent suitable for formulation may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, or the like. In addition, the pharmaceutical composition may further contain a filler, an anti-agglutinating agent, a lubricating agent, a wetting agent, a flavoring agent, an emulsifying agent, a preservative, or the like.

In the method of the present invention, the superoxide dismutase (SOD) may be coated with shellac. When the SOD is administered orally, a problem may arise in that the activity of the SOD is reduced rapidly in the gastrointestinal tract, leading to a decrease in the bioavailability and efficiency thereof. This problem is further exacerbated by the difficulty of delivering the SOD to the particular cell location where the SOD is most effective. Thus, in the method of the present invention, the superoxide dismutase may be coated in solution. Specifically, a purified solution and a shellac-containing solution are mixed with each other, and then freeze-dried. This freeze-dried sample may be powdered and stored at about 4° C. until use. Examples of coatings suitable for use in the present invention include shellac, ethyl cellulose, hydroxypropyl methylcellulose, hydroxypropyl methylcellulose phthalate, zein, Eudragit, and combinations thereof.

The dose of the pharmaceutical composition of the present invention, which contains the *Bacillus amyloliquefaciens* GF423 strain or the *Bacillus amyloliquefaciens* GF424 mutant strain and the SOD produced by this strain, or both, may be suitably determined in consideration of the purpose of treatment or prevention, the type of patient to be prevented or treated, the patient's condition, weight, age or sex, etc. For example, the composition of the present invention may contain, as an active ingredient, the SOD produced by the *Bacillus amyloliquefaciens* GF423 strain, at a therapeutically or nutritionally effective amount, for example, in an amount of 2 to 300 U/mg, based on the total weight of the composition.

The pharmaceutical composition containing the GF-423 strain or the GF-424 mutant strain may generally be administered once or several times as needed, in an amount of $1 \times 10^6$ or more liver bacteria, preferably $1 \times 10^8$ to $1 \times 10^{12}$ live bacteria, for adult patients. Probiotics have a therapeutic effect against inflammatory bowel disease and an excellent ability to adhere to the bowel, and thus may advantageously be used for intestinal drugs or lactic acid bacteria formulations, which are human drugs, as well as feed drugs, health foods, and the like.

Still another aspect of the present invention provides a food, particularly a health functional food, for preventing or ameliorating inflammatory bowel disease, which contains the *Bacillus amyloliquefaciens* GF423 strain (KCTC 13222BP), the *Bacillus amyloliquefaciens* GF424 mutant strain (KCTC 13227BP), or the superoxide dismutase (SOD) derived from this strain. The superoxide dismutase has the amino acid sequence of SEQ ID NO: 1.

As used herein, the term "functional health food" means a processed food refers to a food manufactured and processed from raw materials or components having functionality useful for the human body, and refers to a food that is taken for the purpose of adjusting nutrients with respect to the structure and function of the human body or obtaining the effects useful for the health purposes such as physiologically functional purposes.

The health functional food of the present invention may be prepared and processed in the form of tablets, capsules, powders, granules, liquids, pills, or the like, for the purpose of preventing or ameliorating inflammatory bowel disease. Conventional additives include, for example, chemical synthetic additives, such as ketones, glycine, calcium citrate, nicotinic acid, cinnamic acid, and the like; natural additives, such as persimmon color, licorice extract, crystalline cellulose, kaoliang pigment, guar gum, and the like; and mixed formulations, such as L-sodium glutamate formulations, alkali additives for noodles, preservative formulations, tar color formulations, and the like.

For example, a health functional food in the form of a tablet may be prepared by granulating a mixture of the active ingredient (rebamipide) of the present invention with an excipient, a binder, a disintegrating agent and other additives by a conventional method, and then adding a lubricant, or the like thereto, followed by compression molding, or directly compression-molding the mixture. In addition, the health functional food in the form of a tablet may comprise a corrigent, or the like, if necessary.

Among health functional foods in the form of a capsule, a hard capsule formulation may be prepared by filling a mixture of the active ingredient SOD or strain powder of the present invention with an additive, such as an excipient, into a conventional hard capsule. A soft capsule formulation may be prepared by filling a mixture of the SOD or the strain powder with an additive, such as an excipient, into a capsule such as a gelatin capsule. The soft capsule formulation may, if necessary, contain a plasticizer, such as glycerin or sorbitol, a coloring agent, a preservative, or the like.

A health functional food in the form of a pill may be prepared by molding a mixture of the active ingredient SOD of the present invention with an excipient, a binder, a disintegrant, and the like by a known method. The pill formulation may, if necessary, be coated with white sugar or other coating agent or may also be surface-coated with a substance such as starch or talc.

A health functional food in the form of granule may be prepared in a granular shape by granulating a mixture of the active ingredient SOD of the present invention with an excipient, a binder, a disintegrant, and the like by a known method. The granule formulation may, if necessary, contain a fragrance ingredient, a corrigent, and the like.

The present invention will be described in greater detail below with reference to examples. However, these examples are merely to illustrate the present invention and the scope of the present invention is not limited to these examples.

EXAMPLES

Example 1. Strain Isolation and Identification 1) 16S rRNA Analysis

From *Bacillus polyfermenticus* purchased from Bi-Nex Co., Ltd., a strain was isolated and identified by 16S rDNA sequencing, genomic homology analysis and biochemical features analysis as described below, and as a result, it was identified to belong to *Bacillus amyloliquefaciens*. It was named *Bacillus amyloliquefaciens* GF423 strain.

To identify the *Bacillus amyloliquefaciens* strain, morphological and biochemical examination was first performed, and 16S rDNA sequencing was finally performed. First, for morphological examination, Gram staining was performed, and as a result, the GF423 strain was found to be a Gram-positive *bacillus*. In addition, observation using a phase contrast microscope showed that the strain formed endospores.

To identify the isolated strain, a genome was purified from the isolated strain by the method of Sambrook et al. (Sambrook, J. et al.: "Molecular Cloning. A Laboratory Manual, 3rd ed.," 2001, Cold Spring Harbor Press). The purified genome was sequence using Illumina HiSeq PE100, thereby determining the nucleotide sequence of the entire genome.

different reference strains were found (see Table 1 below). ANI (the average nucleotide identity) and AAI (the average amino acid identity) at genomic level of the found reference strains and the isolated strain were analyzed and verified (Rodriguez-R L. M. & Konstantinidis K. T., https://doi.org/10.7287/peerj.preprints.1900v1 (2016)).

Table 1 below shows the results of analysis of 16S rRNA gene, DDH, ANI and AAI of three different strains which showed the highest homology in DDH analysis with the isolated strain.

TABLE 1

| Reference strain | *Bacillus amyloliquefaciens plantarum* FZB42 | *Bacillus amyloliquefaciens amyloliquefaciens* DSM7 | *Bacillus subtilis spizizenii* NRRL B-23049 | Criteria for species classification |
|---|---|---|---|---|
| 16S rRNA | 99.67 to 99.73% | 99.46 to 99.66% | 99.18 to 99.39% | 98.65% |
| DDH | 92.10% | 78.60% | 32.70% | 70% |
| ANI | 98.65% | 93.59% | 80.04% | 95% |
| AAI | 98.79% | 95.09% | 79.88% | 95% |

The genome of the isolated strain was analyzed, and as a result, 9 copies of 16S rRNA genes (SEQ ID NOs: 2 to 10) were found. Among the 16S rRNA genes, BPJGP_r00130 (SEQ ID NO: 7) and BPJGP_r00160 (SEQ ID NO: 8) showed the same nucleotide sequence, but other 16S rRNA genes showed different nucleotide sequences. Namely, the isolated strain had eight 16S rRNA genes having different nucleotide sequences.

Using the 9 copies of 16S rRNA genes, genus level identification was performed. The 16S rRNA gene database and software used were The Ribosomal Database Project's Classifier (Wang, Q. et al., Appl Environ Microbiol., 73:5261-5267 (2007)), Living Tree Project's Aligner (Pruesse, E. et al., Bioinformatics, 28:1823-1829 (2012)), and EzTaxon database's Identity (Kim, O. S. et al., Int J Syst Evol Microbiol., 62:716721 (2012)). The isolated strain was identified to be a member of the genus *Bacillus* in all types of identification software with a confidence interval of 95% or more.

Species level identification of the isolated strain was performed using the EzTaxon database's Identity (Kim, O. S. et al., Int J Syst Evol Microbiol., 62:716721 (2012)). Although there is currently no international standard for the identity threshold of 16S rRNA for species level identification, 99% which is the highest value of the most widely accepted thresholds (Yarza, P. et al., Nature Rev. Microbiol., 12: 635645 (2014)) was as a search standard. In addition, since the isolated strain had eight different 16S rRNA genes, a search was performed for each of the 16S rRNA genes. Among the found reference strains, the commonly found reference strains were selected. As a result of the search, 80 different reference strains belonging to different species were found. This result is consistent with previous studies indicating that species belonging to the genus *Bacillus* cannot be distinguished using only the homology of 16S rRNA genes (Janda J. M. & Abbott S. L., J Clin Microbiol., 45:2761-2764 (2007); Maughan H. & Van der Auwera G., Infect Genet Evol., 11:789-797 (2011)). Thus, genome-based classification was performed. On the stains selected as described above, the homology of the entire genome of the initially isolated strain was analyzed using in silico DNA-DNA Hybridization (DDH; Auch A. F. et al., Stand Genomic Sci., 28:117-234 (2010)), and reference strains showing a homology of 70% or more were selected. As a result, two Through the comparison of the entire genome of 16S rRNA genes as described above, the isolated strain was identified as a microorganism belonging to *Bacillus amyloliquefaciens*. The isolated strain was named *Bacillus amyloliquefaciens* GF423 and deposited with the Korean Collection for Type Cultures (KCTC), a patent strain depository authority, on Mar. 6, 2017 under accession number KCTC 13222BP.

Example 2. Separation/Purification of Superoxide Dismutase (SOD) from *Bacillus amyloliquefaciens* GF423

2.1 Culturing of *Bacillus amyloliquefaciens* GF423 Strain

For culturing of the *Bacillus amyloliquefaciens* GF423 strain, a single colony formed in LB agar medium (Luria-Bertani (LB) agar; 10 g/L tryptophan, 5 g/L yeast extract, 10 g/L NaCl, 15 g/L agar) was inoculated into 30 ml of LB medium and cultured at 37° C. for 12 hours. The seed culture was inoculated into 3 L of LB medium containing 1 mM manganese sulfate ($MnSO_4$) and was cultured at 37° C. for 20 hours. Then, a portion of the culture was used for the separation of superoxide dismutase. The remaining portion was diluted at $10^{11}$ CFU/ml in phosphate buffered saline (PBS, 10 mM sodium phosphate, 130 mM sodium chloride, pH 7.4) and sonicated, and the supernatant was collected by centrifugation, filtered through a filter having a pore size of 0.45 µm, freeze-dried, and then stored at −20° C. until use in an in vivo experiment.

2.2 Separation and Purification of Superoxide Dismutase

The culture of the *Bacillus amyloliquefaciens* GF423 strain was centrifuged at 3, 578×g at 4° C. for 20 minutes, and the supernatant was collected and concentrated 10-fold by ultrafiltration (MWCO 10,000). Ammonium sulfate was added to 300 ml of the concentrated supernatant to a saturation degree of 60% with stirring at 4° C., followed by stirring for 30 minutes. Then, the supernatant was collected by centrifugation at 3,578×g for 30 minutes, and loaded onto a HiPrep™ Phenyl HP 16/10 column equilibrated with 50 mM potassium phosphate (pH 7.5) containing 2 M ammonium sulfate. Next, elution was performed using 50 mM potassium phosphate (pH 7.5) containing 2 M to 0.1 M ammonium sulfate. The SOD-containing fraction was collected, concentrated by UF (MWCO 10,000), and desalted by dialysis with 50 mM potassium phosphate (pH 7.5). The activity of the superoxide dismutase was analyzed using a superoxide dismutase assay kit (Cayman Chemical, Michigan, USA). One unit of superoxide dismutase activity is defined as the amount of enzyme that inhibits superoxide radicals by 50%. The activity of the purified SOD was 2231.12+269 U/mg, and the molecular weight of the SDS was about 22,000 Dalton.

The superoxide dismutase derived from the *Bacillus amyloliquefaciens* GF423 was coated with the natural coating agent shellac. Shellac was dissolved in 50 mM potassium phosphate (pH 7.0) buffer, mixed with a purified solution of the superoxide dismutase, and freeze-dried. The freeze-dried sample was in a powder form and stored at 4° C.

Example 3. Evaluation of the Effect of Superoxide Dismutase (SOD) Derived from *Bacillus amyloliquefaciens* GF423 or *Bacillus amyloliquefaciens* GF423 Against Inflammatory Bowel Disease 3.1. Production of *Bacillus amyloliquefaciens* GF424 Mutant Strain Using the following primers based on the DNA sequence of *Bacillus amyloliquefaciens* FZB42, sodA gene was cloned by PCR from the genome of *Bacillus amyloliquefaciens* GF423: 5'-gggatgaacacaagtgagag-3'; and 5'-aagctcatgaccacagcaag-3'. The about 2-kb PCR product was cloned using a Mighty TA-cloning kit (Takara) and sequenced using an ABI3730XL DNA analyzer (Applied Biosystems). *Bacillus amyloliquefaciens* AsodA, a strain lacking sodA function, was constructed by double crossover recombination. A pair of DNA fragments adjacent to the sodA gene of *Bacillus amyloliquefaciens* GF423 for homologous recombination was amplified by PCR using the following primers: for the upstream fragment, 5'-aaacagctgggatgaacacaagtgagag-3' and 5'-cacactcttaagtttgcttccaattctggaagtttgtaag-3'; and for the downstream fragment, 5'-ctactgacagcttccaaggatacctgaactaccaaaaccg-3' and 5'-aaacagctgaagctcatgaccacagcaag-3'. Erythromycin resistance (EmR) gene was amplified by PCR on pDG1664 using the following primers: 5'-gaagcaaacttaagagtgtg-3' and 5'-tccttggaagctgtcagtag-3'. The upstream fragment, the EmR gene, and the downstream fragment were assembled in order and cloned into the PvuII site of the plasmid pUori-ts containing a temperature-sensitive replication origin acting in *Bacillus subtilis*. The produced plasmid was transformed into *Bacillus amyloliquefaciens* GF423 by electroporation. A sodA knock-out mutant was selected from transformants having resistance to Em (5 µg/ml) at 42° C., and then plasmid-cured at 30° C. The state of the genome around the sodA site was analyzed by PCR and DNA sequencing of the PCR product. The sodA gene was knocked-out from the genome, and SOD activity in the culture supernatant of the produced knock-out mutant was measured, and as a result, no SOD activity was detected in the sodA knock-out mutant. This suggests that soda is a major extracellular SOD in *Bacillus amyloliquefaciens* GF423.

To improve the expression of the sodA gene, the *Bacillus amyloliquefaciens* GF423 strain was mutated by UV irradiation. From the UV-mutant library, a *Bacillus amyloliquefaciens* GF424 mutant strain having 4.5-fold higher SOD activity than that of the wild-type strain was selected. It was confirmed by sequencing that the sodA gene of *Bacillus amyloliquefaciens* GF424 was the same as that of the wild-type strain. The *Bacillus amyloliquefaciens* GF424 mutant strain was cultured in tryptic soy medium at 37° C. (BD). PCR was performed with Takara's Advantage 2 Polymerase by a standard method.

3.2. Preparation of Test Substances

Test substances for oral administration were prepared as follows. For the preparation of SOD powder, *Bacillus amyloliquefaciens* GF424 was grown in tryptic soy medium at 37° C. for 24 hours. The culture supernatant was collected by centrifugation at 7,500 rpm at 4° C. for 10 minutes. The collected supernatant was filtered through a membrane (Sartorius) having a pore size of 0.25 µm, and then concentrated 10-fold by ultrafiltration using a polyethersulfone membrane (Sartorius) having a fraction molecular weight of 10 kDa.

Enteric coating was performed as follows: the UF concentrate was mixed with the same volume of a 0.1% (w/v) shellac solution dissolved in distilled water and 5% ethanol, and the mixture was freeze-dried. For the preparation of endospores, the *Bacillus amyloliquefaciens* strain was grown in tryptic soy medium at 37° C. for about 48 hours. The precipitate collected by centrifugation at 7,500 rpm at 4° C. for 10 minutes was washed with PBS solution (Sigma), and endospores were purified from the precipitate by the method described by Tavares et al.

3.3. Purification and Protein Analysis 800 ml of the culture supernatant of *Bacillus amyloliquefaciens* GF423 was collected by centrifugation, and filtered and concentrated as described above. Protamine sulfate was added so that the concentrate reached 0.2% (w/v), followed by centrifugation at 12,000 rpm at 4° C. for 45 minutes. After addition of ammonium sulfate at 60% (w/v) or less, the mixture was stirred on ice for 30 minutes and centrifuged, and then the obtained supernatant was precipitated. The supernatant was the ammonium sulfate precipitate was applied to a phenyl-Sepharose HP column (16×10 cm) (GE Healthcare Lie Sciences, USA) equilibrated with 50 mM potassium phosphate buffer (pH 7.5). Protein was eluted with a linear gradient of 2 to 0 M ammonium sulfate equilibrated with 50 mM potassium phosphate buffer. Fractions containing SOD activity were pooled and concentrated with Centricon (Merk, USA) having an MWCO of 10 kD. The concentrate was dialyzed with 50 mM potassium phosphate buffer (pH 7.5). The enzyme purity was measured by SDS-PAGE analysis. The protein was quantified using a Bradford Protein Assay Kit (Biorad, USA). The N-terminus was sequenced by Model 492 protein sequencer (Applied Biosystems, USA). The SOD activity value was 20.24 U/mg (uncoated SOD). The activity of the enteric-coated SOD was 3.64 U/mg.

3.4. Experimental Animals and Diet

6-Week-old female Balb/c (weighing 16 to 20 g) were purchased from Orient-Bio Co. Ltd. (Seongnam, Korea). All the mice were housed in individual cages under specific pathogen-free conditions (temperature: 25±2° C.; humidity: 7% to 75%; illumination: 12-hr light/12-hr dark cycles). All the mice were fed with pellet diet and tap water. This study was approved by the Korea Research Institute of Bioscience and Biotechnology Review Board for the care of animals.

3.5. Oxidative Stress Models and Antioxidant Effect of BA SOD

Mice were randomly divided into nine groups (n=9). The duration of administration was 28 days in all cases. All spores were administered at a dose of $10^7$ CFU/day, and all BA SODs were administered at a dose of 10 U/day in 100 µl of PBS. Oxidative stress was induced by γ-ray irradiation at a dose of 2 Gy every 7 days. A normal control group (NC) and oxidative stress (OS)-induced groups were administered with PBS as a placebo in the same manner. Blood was collected from the mice on the first and last days, incubated at 25° C. for 30 minutes, and centrifuged at 1,300 rpm at 4° C. for 30 minutes. The supernatants were transferred into fresh e-tubes and stored in a deep freezer at −80° C.

TABLE 2

| Groups | Treated strains or SOD | Oxidative stress (OS) |
|---|---|---|
| 1 | PBS | − |
| 2 | Wild-type BA SOD | − |
| 3 | Oxidative stress induction + PBS | + |
| 4 | OS BA SOD | + |
| 5 | BA WT spore (B.a. GF423) | + |
| 6 | BA ΔSODA spore (sodA knock-out mutant) | + |
| 7 | BA HPSOD spore (B.a. GF424) | + |
| 8 | BA WT spore + BA SOD | + |
| 9 | BA HP SOD spore + BA SOD | + |

3.6. Intrarectal Administration of DSS and Induction of Acute Ulcerative Colitis Mice were divided into 8 groups and treated as shown in Table 3 below. 3% DSS (dextran sodium sulfate) dissolved in drinking water was fed to female BALB/c mice for 2 weeks, and then each spore was administered at a dose of $10^7$ CFU/day in 100 µl of PBS for 3 weeks. Each group was treated as follows.

TABLE 3

| Groups | Treated groups or SOD | DSS |
|---|---|---|
| 11 | PBS (Control) | − |
| 12 | PBS | + |
| 13 | BA WT spore (B.a. GF423) | + |
| 14 | BA ΔSOD spore (sodA knockout mutant) | + |
| 15 | BA HP SOD spore (B.a. GF424) | + |
| 16 | BA WT spore + BA SOD | + |
| 17 | BA HP SOD spore + BA SOD | + |
| 18 | BA SOD | + |

As shown in FIGS. 2A and 2B, in the mouse models with DSS-induced ulcerative colitis, the BA SOD, the BA WT spore and the BA HP SOD spore reduced the mortality of the mice, but the BA ΔSODA spore, a sodA knockout mutant, had no effect. FIG. 2 shows the results of the DSS-treated mice. The survival rate was the highest in all the groups treated with the wild-type *Bacillus amyloliquefaciens* GF423 and the SOD high-producing wild-type *Bacillus amyloliquefaciens* GF424 spore (>85%). The survival rates of the mice treated only with the oral SOD, the high-producing spore or the wild-type spore were at least 65%, 55% and 40%, respectively. The mice fed only with DSS or the DSS+BA ΔSODA spore survived at a rate of 30%.

Referring to FIG. 2, the loss rates of the group administered only with DSS and the group administered with the DSS+BA ΔSODA spore were higher than that of the control group. Other groups also had a greater weight loss than the control group, but the loss was less severe (FIGS. 2C and 2D).

3.7. Measurement of Activity Index of Inflammatory Bowel Disease

For each test group, weight loss and the following disease activity index was measured: weight loss, stool consistency, rectal bleeding, and colon length. The results of the measurement are shown in FIG. 3. The disease activity index (DAI) measured according to Cooper et al. (Cooper, Murthy et al. 1993) is a combined index of weight loss, stool consistency and rectal bleeding. The acute clinical syndrome is diarrhea and/or grossly bloody stools. The index is described in Table 4 below.

TABLE 4

| Index | Weight loss | Stool consistency | Rectal bleeding |
|---|---|---|---|
| 0 | None | Solid stool | Normal |
| 1 | 1 to 5% | Soft, semisolid, and does not adhere to the anus | Traces of rectal bleeding |
| 2 | 5 to 10% | Semisolid, but adhere to the rectum | Entire rectal bleeding |
| 3 | 11 to 20% | Liquid and liquid excrement | Traces of rectal/fecal bleeding |
| 4 | 20% | Diarrhea | Entire rectal bleeding |

Figure 3A:
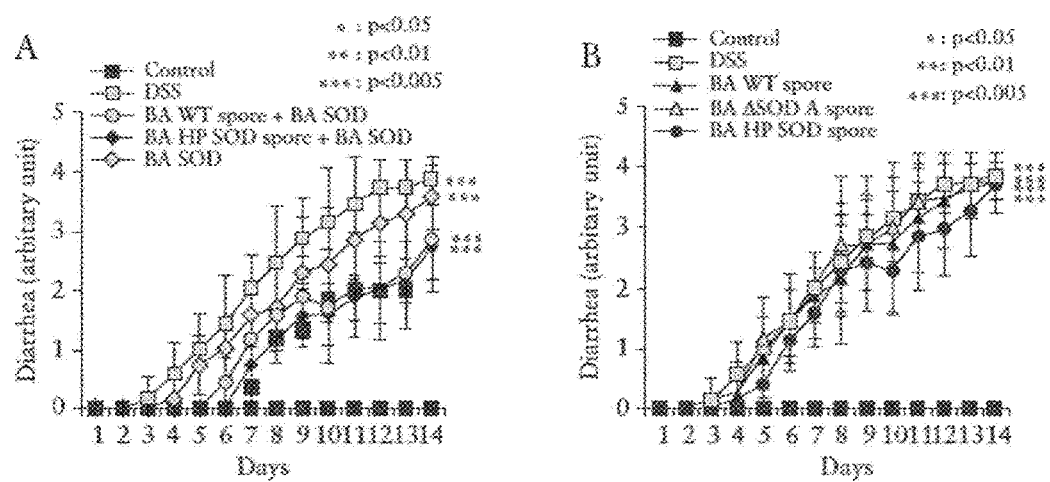
FIGS. 3a to 3c are graphs showing the effects of various test strains and SOD on the diarrhea (FIG. 3a), rectal bleeding (FIG. 3b) and colon length (FIG. 3c) of the DSS-induced colitis mice of each test group after administration.
Figure 3B:
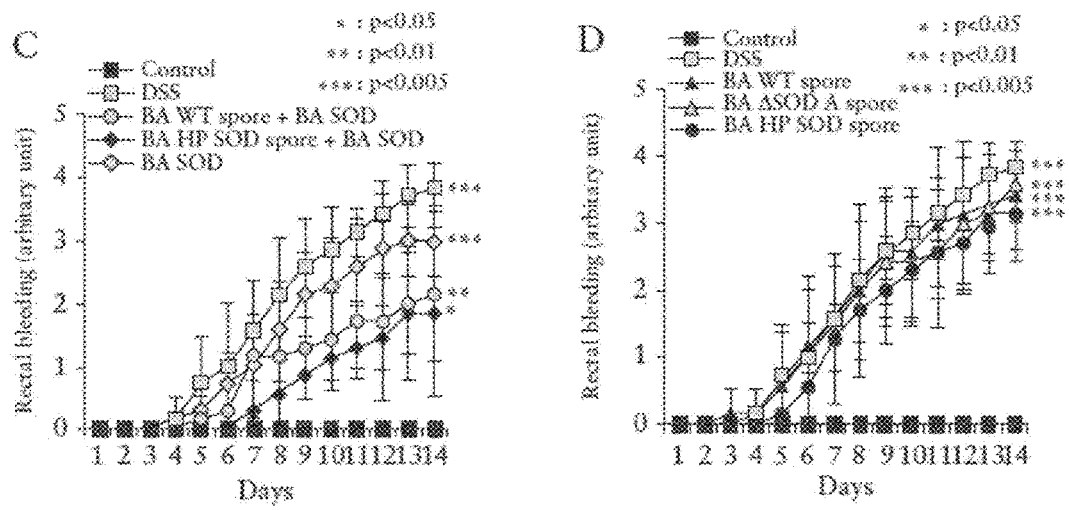
Figure 3C:
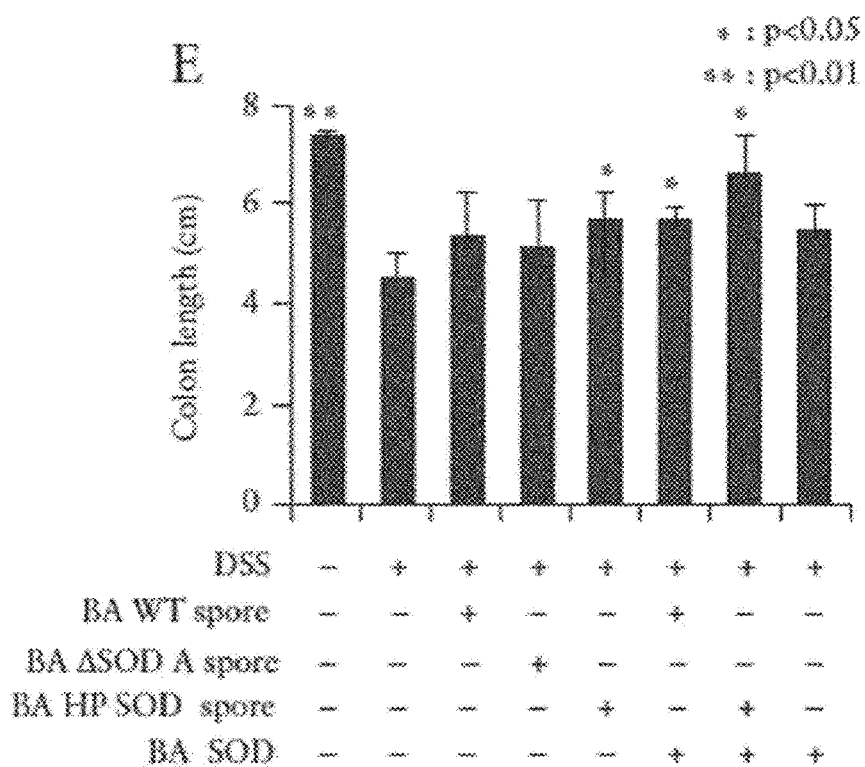

BA SOD and SOD-producing BA spore significantly ameliorated clinical symptoms of DSS-induced colitis, including rectal bleeding (FIG. 3b) and diarrhea (FIG. 3a). The colon length of the group fed only with DSS was shorter than that of the group fed with each of DSS+BA SOD, DSS+BA spore and DSS+BA SOD+BA spore (FIG. 3c). These data show that BA SOD and SOD-producing BA spore ameliorate the development of DSS-induced colitis.

3.8. Histological Analysis

Colon tissue was fixed in 4% formaldehyde, embedded in paraffin, washed with xylene, hydrated, and stained with hematoxylin and eosin (H&E). The colon tissue sections stained with H&E were scored by blind observers based on a previously published system that grades the extent of inflammatory infiltration (0-5), crypt damage (0-4), ulceration (0-3), and the presence or absence of edema. The score shows histological damage associated with DSS treatment in the mid-colon (from the distal end of the plicae to two-thirds of the anus), where inflammation was most severe (see FIG. 4b).

Figure 4A:
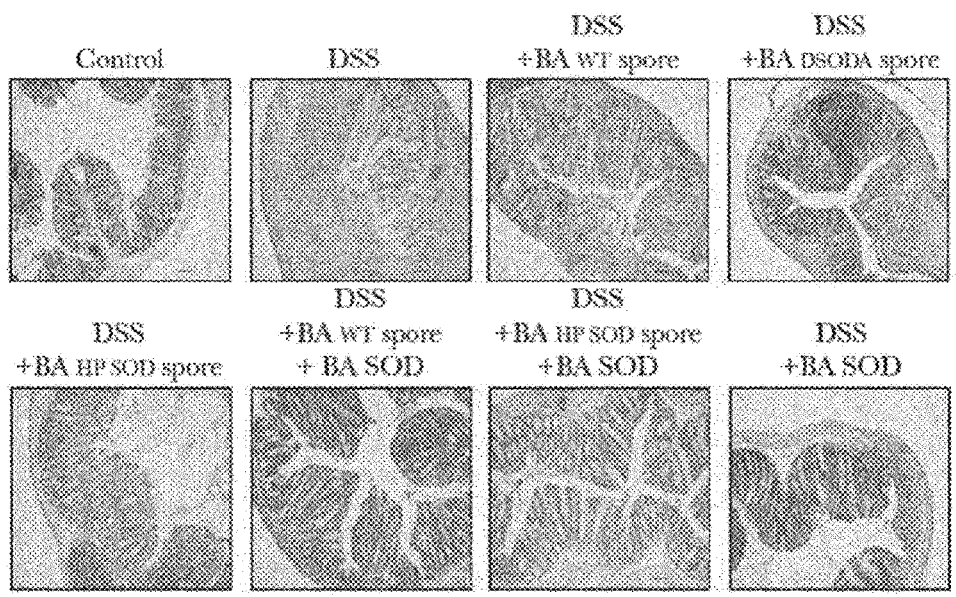
FIG. 4a shows images of colon tissue stained with hematoxylin and eosin to examine effects on mucosal injury in the colitis mice of each test group, and FIG. 4b graphically shows histological score.
Figure 4B:
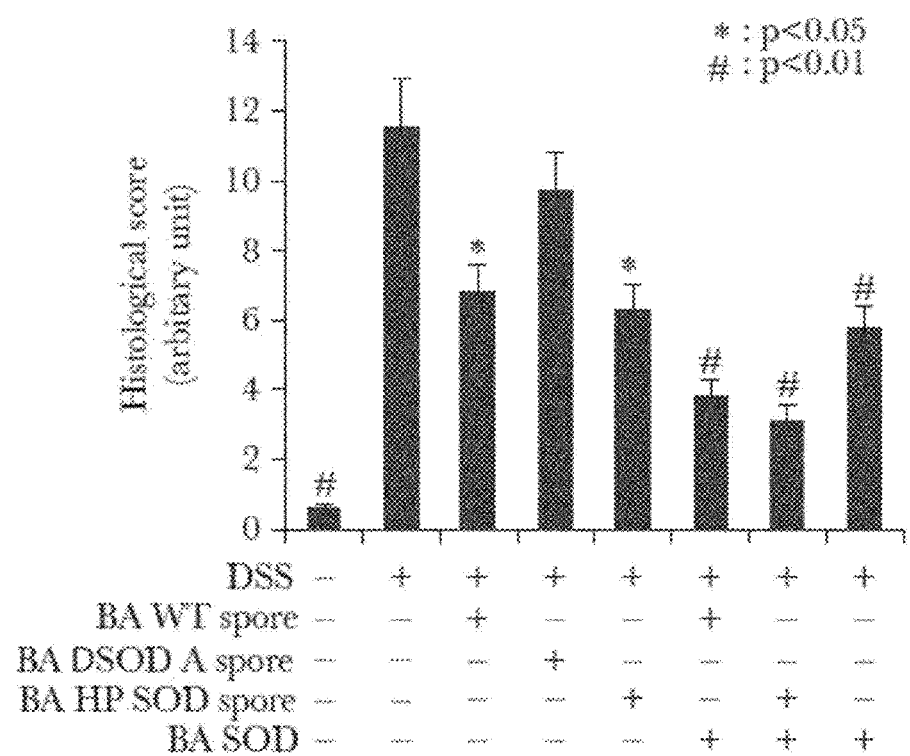

Referring to FIG. 4a, the control group showed histologically normal colon mucosa. In the mice treated only with DDS, colonic mucosa was severely damaged, and highly inflammatory mucosa was observed. Damaged colonic mucosa was also observed in the mice treated with BA ASODA spore. In the mice treated with DSS and BA SOD, BA WT spore and/or BA HPSOD spore, partially damaged colonic mucosa was observed, but the concentration was significantly lower than that in the mice treated with DSS alone (FIG. 4a). In the mice treated with DSS, inflammation was observed in mucosa and submucosa, and mucosa adjacent to the ulcer site had increased edema compared to that in the control mice, and thus cell depletion was severe (FIG. 4(B)). After dietary treatment with BA SOD, BA WT spore and/or BA HPSOD spore, histological analysis revealed a decrease in morphological symptoms of cellular damage. From these data, it can be seen that SOD-producing BA SOD and BA spore reduce mucosal damage in DSS-induced colitis.

3.9. The Effect of BA SOD on Antioxidant Enzyme Activity

The antioxidant effect of BA SOD was evaluated in mouse models with DSS-induced colitis. To examine the antioxidant effect of BA SOD, shellac-coated BA SOD was administered to irradiated, and the degree of change of antioxidant enzymes in the blood was measured. SOD, CAT and GPx activities in the serum samples were measured according to the instructions provided by the kit's supplier (Cayman Chemical Company, Ann Arbor, Mich., USA), and the results of the measurement are shown in FIG. 5.

Figure 5:
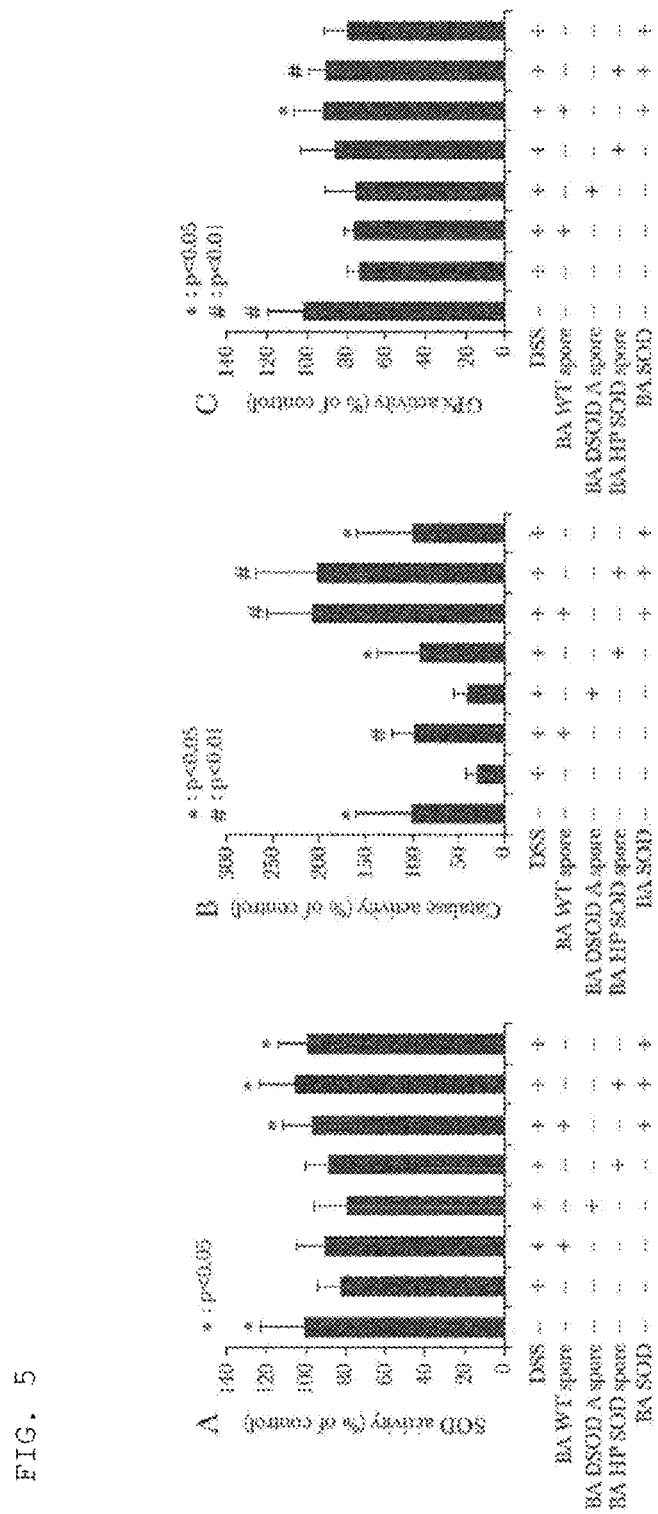
FIG. 5 depicts graphs showing the serum SOD activity (A), catalase activity (B) and glutathione peroxidase (GPx) activity (C) of the DSS-induced colitis mice of each test group.

Referring to FIG. 5, the levels of antioxidants, superoxide dismutase (SOD), catalase (CAT) and glutathione peroxidase (GPx), was higher in the BA SOD group than in the control group. The levels of SOD, CAT and GPx were also higher in the BA WT spore, BA HPSOD spore, BA WT spore+BA SOD, and BA HPSOD spore+BA SOD groups. The levels in the BA ASODA spore group were not influenced.

In contrast, the levels of antioxidant enzymes in the group irradiated with γ-rays were reduced. The levels of the antioxidant enzymes in blood of the BA SOD+irradiation group were restored to levels similar to those of the control group (Table 5). These data show that BA SOD has antioxidant effects and can ameliorate oxidative stress.

Figure 6:
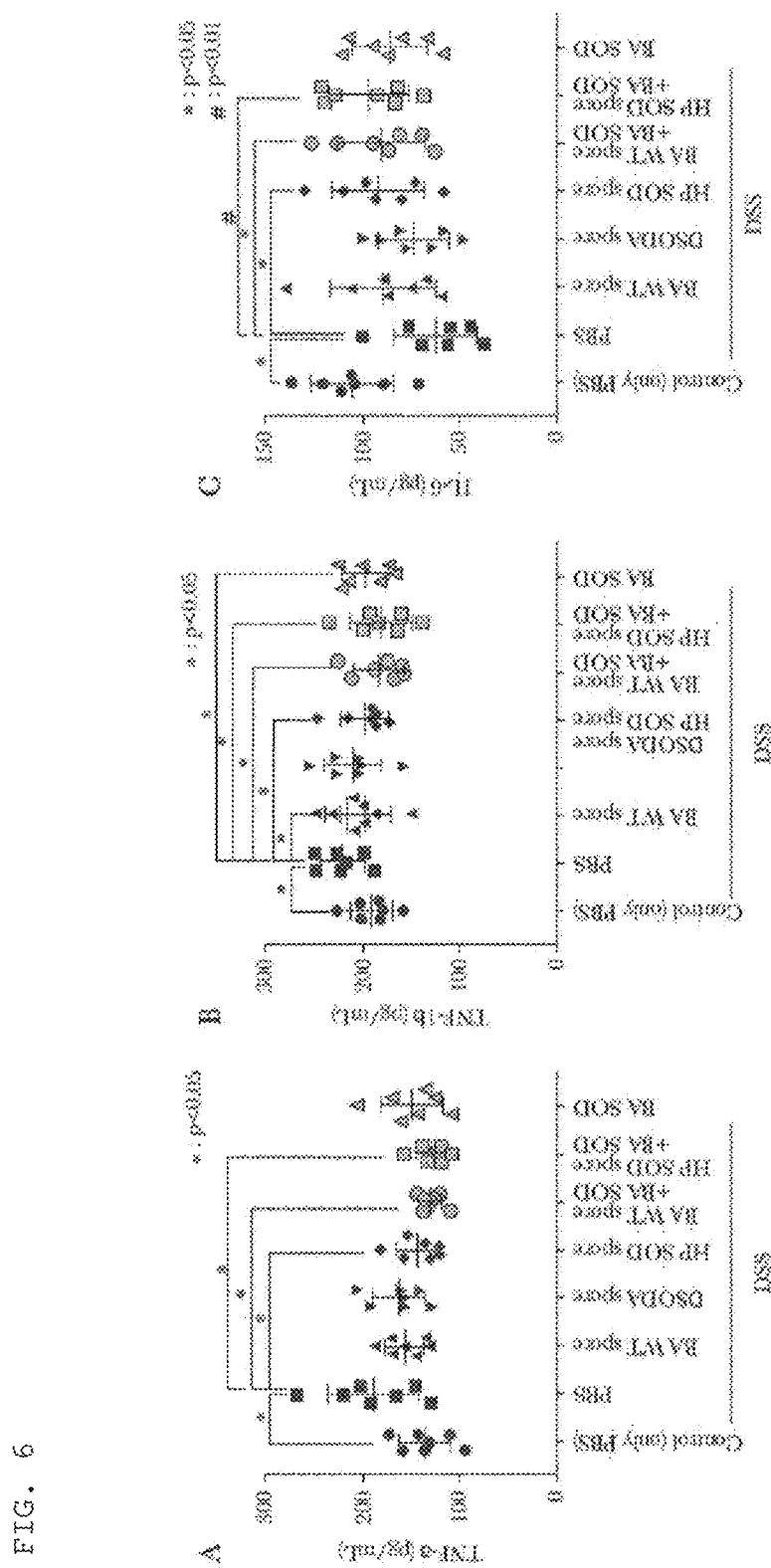
FIG. 6 shows the effect of administration of each test substance against inflammatory cytokines in DSS-induced colitis mice. Specifically.

The levels of pro-inflammatory cytokines, TNFα, and IL1β were higher in the mice fed only with DSS, and were lower in the mice fed with DSS together with BA SOD or BA spore (FIGS. 6A and 6B). The level of the anti-inflammatory cytokine IL6 decreased in the mice fed only with DSS, and increased in the mice fed with DSS together with BA SOD or BA spore (FIGS. 6D and 6C). These data show that BA SOD can ameliorate symptoms of inflammatory bowel disease by increasing the production of anti-inflammatory cytokines.

TABLE 5

| Supplement and condition | Antioxidant enzyme activities | | | | | |
|---|---|---|---|---|---|---|
| | SOD (unit/ml) | | Catalase (nmol/min/ml) | | GPx (nmol/min/ml) | |
| | Day 0 | Day 28 | Day 0 | Day 28 | Day 0 | Day 28 |
| Control | 16.8 ± 0.03 | 19.7 ± 0.03 | 274.06 ± 0.1 | 243.3 ± 0.5 | 3170.4 ± 0.01 | 3146.9 ± 0.07 |
| BA SOD | 15.5 ± 0.05 | 24.9 ± 0.07* | 382.3 ± 0.09 | 555.7 ± 0.1 | 2329.6 ± 0.02 | 2738.2 ± 0.05* |
| γ-irradiation (control) | 14.8 ± 0.1 | 10.8 ± 0.2 | 283.5 ± 0.02 | 141.1 ± 0.03 | 2207.8 ± 0.01 | 117.9 ± 0.05* |
| γ-irradiation + BA SOD | 14.0 ± 0.07 | 18.2 ± 0.2 | 357.9 ± 0.01 | 316.3 ± 0.04* | 1964.0 ± 0.01 | 150.8 ± 0.05 |
| BA WT spore | 14.2 ± 0.33 | 19.9 ± 0.2 | 300.3 ± 0.8 | 447.5 ± 0.69 | 3217.8 ± 0.34 | 3809.9 ± 0.37 |
| BA ΔSODA spore | 14.8 ± 0.13 | 14.7 ± 0.12 | 300. ± 0.24 | 305.2 ± 0.28 | 2821.8 ± 0.11 | 2839.2 ± 0.05 |
| BA HP SOD spore | 14.6 ± 0.14 | 22.5 ± 0.11* | 307.2 ± 0.62 | 550.1 ± 0.14* | 2844.1 ± 0.45 | 3578.4 ± 0.29 |
| BA WT spore + BA SOD | 14.5 ± 0.05 | 26.1 ± 0.14* | 291.2 ± 0.89 | 557.8 ± 0.78* | 3103.1 ± 0.28 | 4132.2 ± 0.13* |
| BA HP SOD spore + BA SOD | 14.8 ± 0.08 | 26.5 ± 0.02* | 320.4 ± 0.72 | 580.2 ± 0.99* | 3905.2 ± 0.22 | 5033.4 ± 0.2* |

BA WT spore: wild-type *Bacillus amyloliquefaciens* GF423;
BA ΔSOD spore: SOD knockout mutant *Bacillus amyloliquefaciens*;
BA HP SOD spore: SOD-high-producing *Bacillus amyloliquefaciens* GF424 mutant strain;
SOD: superoxide dismutase Two-point check on the first and last days. Values are mean±SD (n=7 for each group). Statistical analysis was performed using two-tailed, unpaired Student t-test. Significant differences ($p<0.05$) were compared with each group on day 0.

Referring to FIG. 5, the serum SOD level of the mice fed only with DSS decreased compared to that of the control group, and the antioxidant enzymes in the γ-ray irradiated group also decreased. The SOD level of the mice fed with DSS together with the wild-type *Bacillus amyloliquefaciens* GF423 spore or the BA SOD was higher than that of the mice fed only with DSS (FIG. 5(A). The catalase (CAT) and glutathione peroxidase (GPx) levels of the mice fed only with DSS were lower than those of the control group, but the levels of these antioxidant enzymes in the mice fed with DSS together with BA spore or BA SOD were higher than those in the mice fed only with DSS (FIGS. 5B and 5C). The levels of these antioxidant enzymes in the BA ASODA spore group were not influenced. The levels of the antioxidant enzymes in blood of the BA SOD+irradiation group were restored to levels similar to those of the control group (Table 4). These data show that BA SOD can ameliorate colitis by influencing antioxidant enzymes in vivo.

3.10. Cytokine Analysis

To examine the antioxidant effect of BA SOD, shellac-coated BA SOD was administered to irradiated mice, and the levels of cytokines, IL-1β, TNF-α and IL-6, were measured using a commercial immunoassay kit (R&D System, Minneapolis, Minn., USA) according to the manufacturer's instructions.

3.11. Statistical Analysis

Analysis was performed using Microsoft Excel 2010 for Windows. Quantitative data were expressed as mean±SD. Significance was determined using a two-tailed, unpaired Student's t-test. P-value<0.05 is considered significant.

Although the embodiments of the present invention have been described in detail, this description is only illustrative of a preferred embodiment and is not intended to limit the scope of the present invention. It will be obvious to those skilled in the art that various modifications and changes are possible without departing from the spirit and scope of the present invention. Therefore, the substantial scope of the present invention should be defined by the appended claims and equivalents thereof.

INDUSTRIAL APPLICABILITY

The pharmaceutical composition of the present invention, which contains the *Bacillus amyloliquefaciens* GF423 strain, the superoxide dismutase high-producing *Bacillus amyloliquefaciens* GF424 mutant strain, the superoxide dismutase derived from these strain, and a combination thereof, has excellent antioxidant activity, highly stable enzyme activity, and excellent in vivo stability, and thus may be advantageously used as a material for a pharmaceutical drug, a food, a health supplement food, etc. for preventing or treating inflammatory bowel disease.

The invention claimed is:

1. A pharmaceutical composition for treating inflammatory bowel disease, which contains a superoxide dismutase derived from a *Bacillus amyloliquefaciens* GF423 strain (KCTC 13222BP).

2. A pharmaceutical composition for treating inflammatory bowel disease, which contains a *Bacillus amyloliquefaciens* GF423 strain (KCTC 13222BP) or a superoxide dismutase high-producing *Bacillus amyloliquefaciens* GF424 mutant strain (accession number: KCTC 13227BP).

3. A pharmaceutical composition for treating inflammatory bowel disease, which contains: at least one of a *Bacillus amyloliquefaciens* GF423 strain (KCTC 13222BP) and a superoxide dismutase high-producing *Bacillus amyloliquefaciens* GF424 mutant strain (accession number: KCTC 13227BP); and a superoxide dismutase derived from the *Bacillus amyloliquefaciens* GF423 strain (KCTC 13222BP).

4. The pharmaceutical composition of claim 1, wherein the *Bacillus amyloliquefaciens* GF423 or the *Bacillus amyloliquefaciens* GF424 is one or more selected from the group consisting of a strain, a spore of the strain, a culture of the strain, a concentrate thereof, an extract thereof, and a dried product thereof.

5. The pharmaceutical composition of claim 2, wherein the *Bacillus amyloliquefaciens* GF423 strain or the *Bacillus amyloliquefaciens* GF424 mutant strain is present at a concentration of $1.0 \times 10^7$ CFU/g to $1.0 \times 10^{12}$ CFU/g in the pharmaceutical composition.

6. The pharmaceutical composition of claim 1, wherein the superoxide dismutase has an amino acid sequence of SEQ ID NO: 1.

7. The pharmaceutical composition of claim 1, wherein the superoxide dismutase derived from the *Bacillus amyloliquefaciens* GF423 strain is coated with shellac.

8. The pharmaceutical composition of claim 1, wherein the superoxide dismutase is contained in an amount of 2 to 100 U/mg based on a total weight of the pharmaceutical composition.

9. The pharmaceutical composition of claim 1, wherein the *Bacillus amyloliquefaciens* GF423 strain (KCTC 13222BP) comprises a 16s rRNA gene nucleotide sequence of any one of SEQ ID NOs: 2 to 10.

10. The pharmaceutical composition of claim 1, wherein the inflammatory bowel disease is Crohn's disease or ulcerative colitis.

* * * * *

SEQUENCE LISTING

<160> NUMBER OF SEQ ID NOS: 10

<210> SEQ ID NO 1
<211> LENGTH: 201
<212> TYPE: PRT
<213> ORGANISM: Bacillus amyloliquefaciens

<400> SEQUENCE: 1

```
Met Ala Tyr Lys Leu Pro Glu Leu Pro Tyr Ala Tyr Asp Ala Leu Glu
1               5                   10                  15

Pro His Ile Asp Lys Glu Thr Met Thr Ile His His Thr Lys His His
            20                  25                  30

Asn Thr Tyr Val Thr Asn Leu Asn Lys Ala Ile Glu Gly Ser Ala Leu
        35                  40                  45

Ala Glu Lys Ser Val Asp Glu Leu Val Ala Asp Leu Asn Ala Val Pro
    50                  55                  60

Glu Asp Ile Arg Thr Ala Val Arg Asn Asn Gly Gly Gly His Ala Asn
65                  70                  75                  80

His Ser Leu Phe Trp Thr Leu Leu Ser Pro Asn Gly Gly Gly Glu Pro
                85                  90                  95

Thr Gly Glu Leu Ala Glu Glu Ile Lys Ser Thr Phe Gly Ser Phe Asp
            100                 105                 110

Gln Phe Lys Glu Lys Phe Ala Ala Ala Ala Gly Arg Phe Gly Ser
        115                 120                 125

Gly Trp Ala Trp Leu Val Val Asn Asn Gly Lys Leu Glu Ile Thr Ser
    130                 135                 140

Thr Pro Asn Gln Asp Ser Pro Leu Ser Glu Gly Lys Thr Pro Val Leu
145                 150                 155                 160

Gly Leu Asp Val Trp Glu His Ala Tyr Tyr Leu Asn Tyr Gln Asn Arg
                165                 170                 175

Arg Pro Asp Tyr Ile Ser Ala Phe Trp Asn Val Val Asn Trp Asp Glu
            180                 185                 190

Val Ala Arg Leu Tyr Ser Glu Ala Lys
        195                 200
```

<210> SEQ ID NO 2
<211> LENGTH: 1543
<212> TYPE: DNA
<213> ORGANISM: Bacillus amyloliquefaciens

<400> SEQUENCE: 2

```
agagtttgat cctggctcag gacgaacgct ggcggcgtgc ctaatacatg caagtcgagc    60
ggacagatgg gagcttgctc cctgatgtca gcggcggacg ggtgagtaac acgtgggtaa   120
cctgcctgta agactgggat aactccggga aaccggggct aataccggat ggttgtttga   180
accgcatggt tcagacataa aaggtggctt cggctaccac ttacagatgg acccgcggcg   240
cattagctag ttggtgaggt aacggctcac caaggcaacg atgcgtagcc gacctgagag   300
ggtgatcggc cacactggga ctgagacacg gcccagactc ctacgggagg cagcagtagg   360
gaatcttccg caatggacga aagtctgacg gagcaacgcc gcgtgagtga tgaaggtttt   420
cggatcgtaa agctctgttg ttagggaaga acaagtgccg ttcaaatagg gcggcacctt   480
gacggtacct aaccagaaag ccacggctaa ctacgtgcca gcagccgcgg taatacgtag   540
gtggcaagcg ttgtccggaa ttattgggcg taaagggctc gcaggcggtt tcttaagtct   600
gatgtgaaag ccccccggctc aaccggggag ggtcattgga aactgggaa cttgagtgca   660
```

```
gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttaggggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggtttaa    960
ttcgaagcaa cgcgaagaac cttaccaggt cttgacatcc tctgacaatc ctagagatag   1020
gacgtcccct cgggggcag agtgacaggt ggtgcatggt tgtcgtcagc tcgtgtcgtg   1080
agatgttggg ttaagtcccg caacgagcgc aaccccttgat cttagttgcc agcattcagt   1140
tgggcactct aaggtgactg ccggtgacaa accggaggaa ggtggggatg acgtcaaatc   1200
atcatgcccc ttatgacctg gctacacac gtgctacaat ggacagaaca agggcagcg   1260
aaaccgcgag gttaagccaa tcccacaaat ctgttctcag ttcggatcgc agtctgcaac   1320
tcgactgcgt gaagctggaa tcgctagtaa tcgcggatca gcatgccgcg gtgaatacgt   1380
tcccgggcct tgtacacacc gcccgtcaca ccacgagagt ttgtaacacc cgaagtcggt   1440
gaggtaacct ttatggagcc agccgccgaa ggtgggacag atgattgggg tgaagtcgta   1500
acaaggtagc cgtatcggaa ggtgcggctg gatcacctcc ttt                    1543
```

```
<210> SEQ ID NO 3
<211> LENGTH: 1543
<212> TYPE: DNA
<213> ORGANISM: Bacillus amyloliquefaciens

<400> SEQUENCE: 3
agagtttgat cctggctcag gacgaacgct ggcggcgtgc ctaatacatg caagtcgagc     60
ggacagatgg gagcttgctc cctgatgtta gcggcggacg ggtgagtaac acgtgggtaa    120
cctgcctgta agactgggat aactccggga aaccggggct aatagcggat ggttgtttga    180
accgcatggt tcagacataa aaggtggctt cggctaccac ttacagatgg acccgcggcg    240
cattagctag ttggtgaggt aacggctcac caaggcgacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga acaagtgccg ttcaaatagg gcggcacctt    480
gacggtacct aaccagaaag ccacggctaa ctacgtgcca gcagccgcgg taatacgtag    540
gtggcaagcg ttgtccggaa ttattgggcg taaagggctc gcaggcggtt tcttaagtct    600
gatgtgaaag cccccggctc aaccggggag ggtcattgga aactgggaa cttgagtgca    660
gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttaggggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggtttaa    960
ttcgaagcaa cgcgaagaac cttaccaggt cttgacatcc tctgacaatc ctagagatag   1020
gacgtcccct cgggggcag agtgacaggt ggtgcatggt tgtcgtcagc tcgtgtcgtg   1080
agatgttggg ttaagtcccg caacgagcgc aaccccttgat cttagttgcc agcattcagt   1140
tgggcactct aaggtgactg ccggtgacaa accggaggaa ggtggggatg acgtcaaatc   1200
atcatgcccc ttatgacctg gctacacac gtgctacaat ggacagaaca agggcagcg   1260
```

| | |
|---|---|
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |
| acaaggtagc cgtatcggaa ggtgcggctg atcacctcc ttt | 1543 |

<210> SEQ ID NO 4
<211> LENGTH: 1543
<212> TYPE: DNA
<213> ORGANISM: Bacillus amyloliquefaciens

<400> SEQUENCE: 4

| | |
|---|---|
| agagtttgat cctggctcag gacgaacgct ggcggcgtgc ctaatacatg caagtcgagc | 60 |
| ggacagatgg gagcttgctc cctgatgtta gcggcggacg ggtgagtaac acgtgggtaa | 120 |
| cctgcctgta agactgggat aactccggga aaccggggct aataccggat ggttgtctga | 180 |
| accgcatggt tcagacataa aaggtggctt cggctaccac ttacagatgg acccgcggcg | 240 |
| cattagctag ttggtgaggt aacggctcac caaggcgacg atgcgtagcc gacctgagag | 300 |
| ggtgatcggc cacactggga ctgagacacg gcccagactc ctacgggagg cagcagtagg | 360 |
| gaatcttccg caatggacga aagtctgacg agcaacgcc gcgtgagtga tgaaggtttt | 420 |
| cggatcgtaa agctctgttg ttagggaaga acaagtgccg ttcaaatagg gcggcacctt | 480 |
| gacggtacct aaccagaaag ccacggctaa ctacgtgcca gcagccgcgg taatacgtag | 540 |
| gtggcaagcg ttgtccggaa ttattgggcg taaagggctc gcaggcggtt tcttaagtct | 600 |
| gatgtgaaag cccccggctc aaccggggag ggtcattgga aactgggaa cttgagtgca | 660 |
| gaagaggaga gtggaattcc acgtgtagcg gtgaaatgcg tagagatgtg gaggaacacc | 720 |
| agtggcgaag gcgactctct ggtctgtaac tgacgctgag gagcgaaagc gtggggagcg | 780 |
| aacaggatta gataccctgg tagtccacgc cgtaaacgat gagtgctaag tgttaggggg | 840 |
| tttccgcccc ttagtgctgc agctaacgca ttaagcactc cgcctgggga gtacggtcgc | 900 |
| aagactgaaa ctcaaaggaa ttgacggggg cccgcacaag cggtggagca tgtggtttaa | 960 |
| ttcgaagcaa cgcgaagaac cttaccaggt cttgacatcc tctgacaatc ctagagatag | 1020 |
| gacgtcccct cggggggcag agtgacaggt ggtgcatggt tgtcgtcagc tcgtgtcgtg | 1080 |
| agatgttggg ttaagtcccg caacgagcgc aacccttgat cttagttgcc agcattcagt | 1140 |
| tgggcactct aaggtgactg ccggtgacaa accggaggaa ggtggggatg acgtcaaatc | 1200 |
| atcatgcccc ttatgacctg gctacacac gtgctacaat ggacagaaca aagggcagcg | 1260 |
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |
| acaaggtagc cgtatcggaa ggtgcggctg atcacctcc ttt | 1543 |

<210> SEQ ID NO 5
<211> LENGTH: 1543
<212> TYPE: DNA
<213> ORGANISM: Bacillus amyloliquefaciens

<400> SEQUENCE: 5

```
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtttga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt cttaagtct      600 gatgtgaaag cccccggctc aaccggggag ggtcattgga aactgggaa cttgagtgca     660 gaagaggaga gtggaattcc acgtgtagcg gtgaaatgcg tagagatgtg gaggaacacc     720
agtggcgaag gcgactctct ggtctgtaac tgacgctgag gagcgaaagc gtggggagcg     780
aacaggatta gataccctgg tagtccacgc cgtaaacgat gagtgctaag tgttaggggg     840
tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020
gacgtcccct cgggggcag agtgacaggt ggtgcatggt tgtcgtcagc tcgtgtcgtg    1080
agatgttggg ttaagtcccg caacgagcgc aacccttgat cttagttgcc agcattcagt    1140
tgggcactct aaggtgactg ccggtgacaa accggaggaa ggtggggatg acgtcaaatc    1200
atcatgcccc ttatgacctg gctacacacg tgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct ttatggagcc agccgccgaa ggtgggacag atgattgggg tgaagtcgta    1500
acaaggtagc cgtatcggaa ggtgcggctg gatcacctcc ttt                      1543
```

<210> SEQ ID NO 6
<211> LENGTH: 1543
<212> TYPE: DNA
<213> ORGANISM: Bacillus amyloliquefaciens

<400> SEQUENCE: 6

```
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtctga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt cttaagtct      600
```

```
gatgtgaaag cccccggctc aaccggggag ggtcattgga aactggggaa cttgagtgca      660
gaagaggaga gtggaattcc acgtgtagcg gtgaaatgcg tagagatgtg gaggaacacc      720
agtggcgaag gcgactctct ggtctgtaac tgacgctgag gagcgaaagc gtggggagcg      780
aacaggatta gataccctgg tagtccacgc cgtaaacgat gagtgctaag tgttaggggg      840
tttccgcccc ttagtgctgc agctaacgca ttaagcactc cgcctgggga gtacggtcgc      900
aagactgaaa ctcaaaggaa ttgacggggg cccgcacaag cggtggagca tgtggtttaa      960
ttcgaagcaa cgcgaagaac cttaccaggt cttgacatcc tctgacaatc ctagagatag     1020
gatgtcccct tcgggggcag agtgacaggt ggtgcatggt tgtcgtcagc tcgtgtcgtg     1080
agatgttggg ttaagtcccg caacgagcgc aacccttgat cttagttgcc agcattcagt     1140
tgggcactct aaggtgactg ccggtgacaa accggaggaa ggtggggatg acgtcaaatc     1200
atcatgcccc ttatgacctg gctacacacg tgctacaatg gacagaaaca agggcagcg      1260 aaaccgcgag gttaagccaa tcccacaaat ctgttctcag ttcggatcgc agtctgcaac     1320
tcgactgcgt gaagctggaa tcgctagtaa tcgcggatca gcatgccgcg gtgaatacgt     1380
tcccgggcct tgtacacacc gcccgtcaca ccacgagagt ttgtaacacc cgaagtcggt     1440
gaggtaaccc ttatggagcc agccgccgaa ggtgggacag atgattgggg tgaagtcgta     1500
acaaggtagc cgtatcggaa ggtgcggctg gatcacctcc ttt                       1543

<210> SEQ ID NO 7
<211> LENGTH: 1543
<212> TYPE: DNA
<213> ORGANISM: Bacillus amyloliquefaciens

<400> SEQUENCE: 7
agagtttgat cctggctcag gacgaacgct ggcggcgtgc ctaatacatg caagtcgagc       60
ggacagatgg gagcttgctc cctgatgtta gcggcggacg ggtgagtaac acgtgggtaa      120
cctgcctgta agactgggat aactccggga aaccggggct aataccggat ggttgtctga      180
accgcatggt tcagacataa aaggtggctt cggctaccac ttacagatgg acccgcggcg      240
cattagctag ttggtgaggt aacggctcac caaggcgacg atgcgtagcc gacctgagag      300
ggtgatcggc cacactggga ctgagacacg gcccagactc ctacgggagg cagcagtagg      360
gaatcttccg caatggacga aagtctgacg gagcaacgcc gcgtgagtga tgaaggtttt      420
cggatcgtaa agctctgttg ttagggaaga acaagtgccg ttcaaatagg cggcaccctt      480
gacggtacct aaccagaaag ccacggctaa ctacgtgcca gcagccgcgg taatacgtag      540
gtggcaagcg ttgtccggaa ttattgggcg taaagggctc gcaggcggtt cttaagtct      600 gatgtgaaag cccccggctc aaccggggag ggtcattgga aactggggaa cttgagtgca      660
gaagaggaga gtggaattcc acgtgtagcg gtgaaatgcg tagagatgtg gaggaacacc      720
agtggcgaag gcgactctct ggtctgtaac tgacgctgag gagcgaaagc gtggggagcg      780
aacaggatta gataccctgg tagtccacgc cgtaaacgat gagtgctaag tgttaggggg      840
tttccgcccc ttagtgctgc agctaacgca ttaagcactc cgcctgggga gtacggtcgc      900
aagactgaaa ctcaaaggaa ttgacggggg cccgcacaag cggtggagca tgtggtttaa      960
ttcgaagcaa cgcgaagaac cttaccaggt cttgacatcc tctgacaatc ctagagatag     1020
gatgtcccct tcgggggcag agtgacaggt ggtgcatggt tgtcgtcagc tcgtgtcgtg     1080
agatgttggg ttaagtcccg caacgagcgc aacccttgat cttagttgcc agcattcagt     1140
```

| | |
|---|---|
| tgggcactct aaggtgactg ccggtgacaa accggaggaa ggtggggatg acgtcaaatc | 1200 |
| atcatgcccc ttatgacctg gctacacacg tgctacaat ggacagaaca aagggcagcg | 1260 |
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |
| acaaggtagc cgtatcggaa ggtgcggctg gatcacctcc ttt | 1543 |

<210> SEQ ID NO 8
<211> LENGTH: 1543
<212> TYPE: DNA
<213> ORGANISM: Bacillus amyloliquefaciens

<400> SEQUENCE: 8

| | |
|---|---|
| agagtttgat cctggctcag gacgaacgct ggcggcgtgc ctaatacatg caagtcgagc | 60 |
| ggacagatgg gagcttgctc cctgatgtta gcggcggacg ggtgagtaac acgtgggtaa | 120 |
| cctgcctgta agactgggat aactccggga aaccggggct aataccggat ggttgtttga | 180 |
| accgcatggt tcagacataa aagtggcttc ggctaccac ttacagatgg acccgcggcg | 240 |
| cattagctag ttggtgaggt aacggctcac caaggcaacg atgcgtagcc gacctgagag | 300 |
| ggtgatcggc cacactggga ctgagacacg gcccagactc ctacgggagg cagcagtagg | 360 |
| gaatcttccg caatggacga aagtctgacg gagcaacgcc gcgtgagtga tgaaggtttt | 420 |
| cggatcgtaa agctctgttg ttagggaaga acaagtgccg ttcaaatagg gcggcacctt | 480 |
| gacggtacct aaccagaaag ccacggctaa ctacgtgcca gcagccgcgg taatacgtag | 540 |
| gtggcaagcg ttgtccggaa ttattgggcg taaagggctc gcaggcggtt cttaagtct | 600 |
| gatgtgaaag cccccggctc aaccggggag ggtcattgga aactggggaa cttgagtgca | 660 |
| gaagaggaga gtggaattcc acgtgtagcg gtgaaatgcg tagagatgtg gaggaacacc | 720 |
| agtggcgaag gcgactctct ggtctgtaac tgacgctgag gagcgaaagc gtggggagcg | 780 |
| aacaggatta gataccctgg tagtccacgc cgtaaacgat gagtgctaag tgttaggggg | 840 |
| tttccgcccc ttagtgctgc agctaacgca ttaagcactc cgcctgggga gtacggtcgc | 900 |
| aagactgaaa ctcaaaggaa ttgacggggg cccgcacaag cggtggagca tgtggtttaa | 960 |
| ttcgaagcaa cgcgaagaac cttaccaggt cttgacatcc tctgacaatc ctagagatag | 1020 |
| gacgtcccct tcgggggcag agtgacaggt ggtgcatggt tgtcgtcagc tcgtgtcgtg | 1080 |
| agatgttggg ttaagtcccg caacgagcgc aaccttgat cttagttgcc agcattcagt | 1140 |
| tgggcactct aaggtgactg ccggtgacaa accggaggaa ggtggggatg acgtcaaatc | 1200 |
| atcatgcccc ttatgacctg gctacacacg tgctacaat ggacagaaca aagggcagcg | 1260 |
| aaaccgcgag gttaagccaa tcccacaaat ctgttctcag ttcggatcgc agtctgcaac | 1320 |
| tcgactgcgt gaagctggaa tcgctagtaa tcgcggatca gcatgccgcg gtgaatacgt | 1380 |
| tcccgggcct tgtacacacc gcccgtcaca ccacgagagt ttgtaacacc cgaagtcggt | 1440 |
| gaggtaacct ttatggagcc agccgccgaa ggtgggacag atgattgggg tgaagtcgta | 1500 |
| acaaggtagc cgtatcggaa ggtgcggctg gatcacctcc ttt | 1543 |

<210> SEQ ID NO 9
<211> LENGTH: 1543
<212> TYPE: DNA
<213> ORGANISM: Bacillus amyloliquefaciens

<400> SEQUENCE: 9

```
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtctga     180
atcgcatggt tcagacataa aaggtggctt ctgctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
gacggtacct aaccagaaag ccacggctaa ctacgtgcca gcagccgcgg taatacgtag     540
gtggcaagcg ttgtccggaa ttattgggcg taaagggctc gcaggcggtt tcttaagtct     600
gatgtgaaag cccccggctc aaccggggag ggtcattgga aactgggaa cttgagtgca     660
gaagaggaga gtggaattcc acgtgtagcg gtgaaatgcg tagagatgtg gaggaacacc     720
agtggcgaag gcgactctct ggtctgtaac tgacgctgag gagcgaaagc gtggggagcg     780
aacaggatta gataccctgg tagtccacgc cgtaaacgat gagtgctaag tgttaggggg     840
tttccgcccc ttagtgctgc agctaacgca ttaagcactc cgcctgggga gtacggtcgc     900
aagactgaaa ctcaaaggaa ttgacggggg cccgcacaag cggtggagca tgtggtttaa     960
ttcgaagcaa cgcgaagaac cttaccaggt cttgacatcc tctgacaatc ctagagatag    1020
gacgtcccct tcggggcag agtgacaggt ggtgcatggt tgtcgtcagc tcgtgtcgtg    1080
agatgttggg ttaagtcccg caacgagcgc aaccccttgat cttagttgcc agcattcagt    1140
tgggcactct aaggtgactg ccggtgacaa accggaggaa ggtggggatg acgtcaaatc    1200
atcatgcccc ttatgacctg ggctacacac gtgctacaat ggacagaaca aagggcagcg    1260
aaaccgcgag gttaagccaa tcccacaaat ctgttctcag ttcggatcgc agtctgcaac    1320
tcgactgcgt gaagctggaa tcgctagtaa tcgcggatca gcatgccgcg gtgaatacgt    1380
tcccgggcct tgtacacacc gcccgtcaca ccacgagagt ttgtaacacc cgaagtcggt    1440
gaggtaacct tttaggagcc agccgccgaa ggtgggacag atgattgggg tgaagtcgta    1500
acaaggtagc cgtatcggaa ggtgcggctg atcacctcc ttt                       1543
```

<210> SEQ ID NO 10
<211> LENGTH: 1543
<212> TYPE: DNA
<213> ORGANISM: Bacillus amyloliquefaciens

<400> SEQUENCE: 10

```
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccagat ggttgtctga     180
accgcatggt tcagacataa aaggtggctt cggctaccac ttacagatgg acccgcggcg     240
cattagctag ttggtgaggt aacggctcac caaggcgacg atgcgtagcc gacctgagag     300
ggtgatcggc cacactggga ctgagacacg gcccagactc ctacgggagg cagcagtagg     360
gaatcttccg caatggacga aagtctgacg gagcaacgcc gcgtgagtga tgaaggtttt     420
cggatcgtaa agctctgttg ttagggaaga acaagtgccg ttcaaatagg gcggcacctt     480
```

```
                                                       -continued gacggtacct aaccagaaag ccacggctaa ctacgtgcca gcagccgcgg taatacgtag    540
gtggcaagcg ttgtccggaa ttattgggcg taaagggctc gcaggcggtt tcttaagtct    600
gatgtgaaag cccccggctc aaccggggag ggtcattgga aactggggaa cttgagtgca    660
gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttaggggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggtttaa    960
ttcgaagcaa cgcgaagaac cttaccaggt cttgacatcc tctgacaatc ctagagatag   1020
gacgtcccct tcgggggcag agtgacaggt ggtgcatggt tgtcgtcagc tcgtgtcgtg   1080
agatgttggg ttaagtcccg caacgagcgc aaccctTgat cttagttgcc agcattcagt   1140
tgggcactct aaggtgactg ccggtgacaa accggaggaa ggtggggatg acgtcaaatc   1200
atcatgcccc ttatgacctg ggctacacac gtgctacaat ggacagaaca aagggcagcg   1260
aaaccgcgag gttaagccaa tcccacaaat ctgttctcag ttcggatcgc agtctgcaac   1320
tcgactgcgt gaagctggaa tcgctagtaa tcgcggatca gcatgccgcg gtgaatacgt   1380
tcccgggcct tgtacacacc gcccgtcaca ccacgagagt ttgtaacacc cgaagtcggt   1440
gaggtaacct tttaggagcc agccgccgaa ggtgggacag atgattgggg tgaagtcgta   1500
acaaggtagc cgtatcggaa ggtgcggctg gatcacctcc ttt                     1543
```